(12) United States Patent
Miller et al.

(10) Patent No.: US 8,846,989 B2
(45) Date of Patent: *Sep. 30, 2014

(54) METHOD OF PRODUCING ALCOHOLS

(75) Inventors: Jorge Miller, Houston, TX (US); Luisa Kling Miller, Houston, TX (US)

(73) Assignee: Sajet Development LLC, Houston, TX (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/369,255

(22) Filed: Feb. 8, 2012

(65) Prior Publication Data

US 2012/0142977 A1 Jun. 7, 2012

Related U.S. Application Data

(63) Continuation-in-part of application No. 13/308,443, filed on Nov. 30, 2011, now abandoned, which is a continuation-in-part of application No. 12/927,936, filed on Nov. 30, 2010, now Pat. No. 8,227,647.

(60) Provisional application No. 61/336,962, filed on Jan. 28, 2010, provisional application No. 61/283,167, filed on Nov. 30, 2009.

(51) Int. Cl.
C07C 29/54 (2006.01)
C07C 67/11 (2006.01)
C07C 17/10 (2006.01)
C07C 29/09 (2006.01)

(52) U.S. Cl.
CPC ............... *C07C 67/11* (2013.01); *C07C 29/54* (2013.01); *C07C 17/10* (2013.01); *C07C 29/095* (2013.01)
USPC ............... 568/911; 568/910; 568/910.5

(58) Field of Classification Search
CPC ................................................ C07C 29/54
USPC ........................... 568/911, 910, 910.5
See application file for complete search history.

(56) References Cited

U.S. PATENT DOCUMENTS

2011/0130597 A1    6/2011    Miller

*Primary Examiner* — Elvis O Price
(74) *Attorney, Agent, or Firm* — McDermott Will & Emery LLP

(57) ABSTRACT

A method of making alcohols involves forming of alcohol esters from liquid alkane halides and a solution of metallic salts of organic acids to produce gaseous alcohol esters for reaction with magnesium or metal hydroxides to form the alcohol and the metal salt of the organic acids. In an improvement method liquid phase alcohol esters instead of gaseous alcohol esters are produced from liquid alkane halides and a solution of metal salts of organic acids whose alkane esters are less soluble in water than that of the alkane halide and treating of the alcohol ester formed with magnesium or metal hydroxides to form the alcohol and the metal salt of the organic acids.

16 Claims, 3 Drawing Sheets

METHOD OF PRODUCING ALCOHOLS

RELATED APPLICATIONS

This application claims priority to U.S. application Ser. No. 12/927,936 filed Nov. 30, 2010, which claims priority to U.S. Provisional Application Nos. 61/283,167 filed on Nov. 30, 2009; and 61/336,962, filed on Jan. 28, 2010, the disclosures of which are each incorporated herein by reference.

TECHNICAL FIELD

The disclosure relates to a method of making alcohols, and more specifically alkanols, from alkanes, and more specifically from alkane halides.

BACKGROUND

Alcohols are industrially produced from direct hydration of alkenes, such as ethylene, or from cracking of appropriate fractions of distilled (or fractionated) crude oil. While demands for alcohols, and especially for ethanol, continue to increase, crude oil reserves continue to be depleted. Moreover, the processes of alkene hydration and fractionation and cracking of crude oil are themselves energy intensive processes.

There remains a need therefore, for a method of producing alcohols from more readily available starting materials and for a process which does not require the energy input necessary for current industrial alcohol production.

SUMMARY OF THE DISCLOSURE

The disclosure provides a method of making alcohols. More specifically, an illustrative disclosed method comprises reacting an alkane gas with a halogen gas in a halogenation reactor to form a halogenation reaction product mixture comprising alkane halide and hydrogen halide mixture; contacting the halogenation reaction product mixture with a metal organic salt thereby forming an extractor product mixture of a metal halide, organic ester, and organic acid; separating the organic ester and organic acid mixture from the metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the organic ester and organic acid mixture to form a raw product comprising alkanol and a metal organic salt.

In an improvement method of making alcohols, the disclosed method involves liquid phase forming of alcohol esters from liquid alkane halides and a solution of metal salts of organic acids whose alkanes esters are less soluble in water than that of the alkane halide and treating of the alcohol ester formed with magnesium or metal hydroxides to form the alcohol and the metal salt of the organic acids.

BRIEF DESCRIPTION OF THE DRAWINGS

The drawings illustrate an exemplary form of the disclosure; it being understood, however, that this disclosure is not limited to the precise arrangements and instrumentalities shown in the drawing.

DETAILED DESCRIPTION

Figure 1:
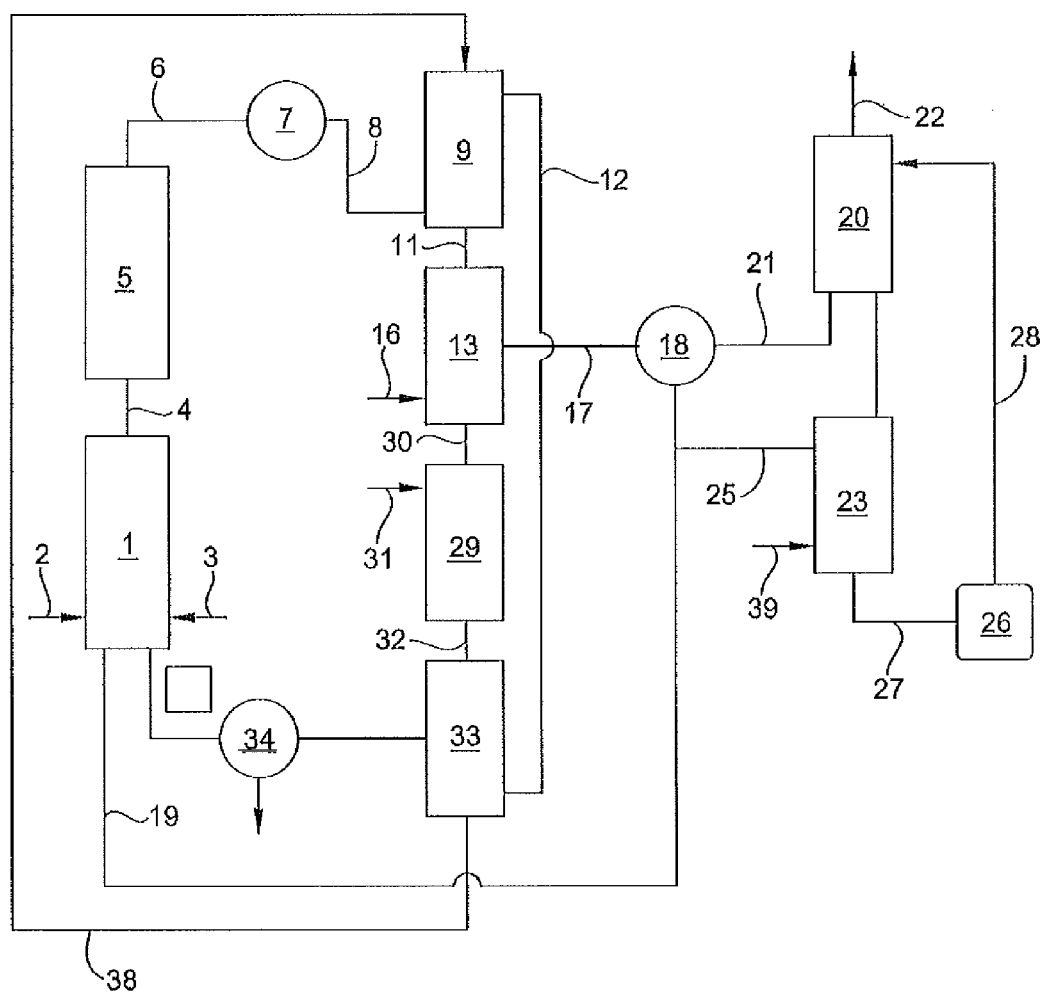
FIG. 1 is a schematic diagram of one embodiment of the disclosed process.

The disclosure is a method for making alcohols. The disclosure is a method for producing organic alcohols, including for example, methanol, ethanol, propanol, and combinations thereof.

In one illustrative embodiment, the instant disclosure provides a method comprising: reacting an alkane with a halogen gas in a halogenations reactor to form a halogenation reaction product mixture comprising alkane halide and hydrogen halide mixture; contacting the halogenation reaction product mixture with a metal organic salt thereby forming an extractor product mixture of a metal halide, organic salt, organic ester, and organic acid; separating the organic ester and organic acid mixture from the metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the organic ester and organic acid mixture to form a raw product comprising alkanol and a metal organic salt.

In an alternative illustrative improvement embodiment, the instant disclosure provides a method comprising: reacting an alkane with a halogen gas in a halogenations reactor to form a halogenation reaction product mixture comprising alkane halide and hydrogen halide mixture; contacting the halogenation reaction product mixture with a metal organic salt under aqueous conditions thereby forming an aqueous extractor product mixture of a soluble metal halide, and an insoluble organic ester; separating the insoluble organic ester from the aqueous metal halide; oxygenating the metal halide to form a metal oxide and halide containing gasses; separating the metal oxide from the halide containing gasses; mixing the metal oxide with water to form a metal oxide slurry; mixing the metal oxide slurry with a countercurrent flow of the insoluble organic ester and insoluble organic salt mixture to form a raw product comprising alkanol.

In yet another alternative illustrative improvement method of making alcohols, the instant disclosure provides a method for the production of alcohols comprising: contacting an alkane gas with an aqueous halide saturated solution to strip the halide from the solution to form a product mixture of an alkane and a halide; reacting a halogen gas with the alkane halide mixture to form an alkyl halide, an alkyl di halide, an alkyl tri halide, and a hydrogen halide gasses; neutralizing the alkyl di halide, the alkyl tri halide, and the hydrogen halide gasses with a suspension of magnesium hydroxide; cooling the gasses from the neutralizing step to a temperature to liquefy the gasses to form liquefied gasses; mixing the liquefied gasses with a magnesium benzoate or butyrate solution to form an aqueous solution of benzoate or butyrate ethyl esters; separating the benzoate or butyrate ethyl esters in the aqueous solution which are water insoluble from water in the aqueous solution to form an ester insoluble layer comprising benzoate or butyrate ethyl esters and a water layer containing magnesium halide; contacting the ester insoluble layer with a suspension of magnesium hydroxide to form an alcohol.

Alkanes useful in various embodiments of the disclosed methods may be selected from the group consisting of C1-C20 alkanes, including most preferably, methane, ethane, propane, butane and mixtures thereof. All combinations and subcombinations of such alkanes are included and disclosed herein. For example, the alkanes may comprise a mixture of methane and ethane; or in the alternative, a mixture of methane and propane; or in the alternative, a mixture of ethane and butane. In the alternative, the alkane may comprise only a single alkane. For example, the alkane may comprise methane with no other alkane component; or in the alternative, the alkane may comprise ethane with no other alkane component; or in the alternative the alkane may comprise propane with no other alkane component.

Halogen gasses useful in various embodiments of the disclosed methods may be selected from the group consisting of chlorine gas, bromine gas, iodine gas, and combinations thereof. All combinations and subcombinations of such halogen gasses are included and disclosed herein. For example, the halogen gasses may comprise a mixture of chlorine and bromine gasses; or in the alternative the halogen gasses may comprise a mixture of chlorine and iodine gasses. In the alternative, the halogen gas useful in the halogenations step of the disclosed method may comprise only a single halogen gas. For example the halogen gas may be bromine gas; or in the alternative, the halogen gas may be chlorine gas. The halogen gas or gasses used in the halogenation reactor may be supplied directly into the halogenations reactor, as for example, by injection through a dedicated supply line. Alternatively, the halogen gas or gasses used in the halogenation reactor may be formed in situ in the halogenation reactor.

Metal organic salts useful in the disclosed method of FIG. 1 may be selected from the group consisting of metal formate, metal acetate, metal benzoate, and combinations thereof. The metal of the metal organic salt in various embodiments of the disclosed method of FIG. 1 may be selected from Magnesium, Zinc, and combinations thereof, for example. All combinations and subcombinations of the metal organic salts are disclosed and included herein. For example, the metal organic salt may be magnesium formate, zinc acetate, magnesium benzoate, zinc dichlorobenzoate, zinc dichloroacetate, or any combination of two or more of the foregoing. Metal organic salts useful in the improvement methods disclosed below are selected based on the water solubility of the alkane halide with which the metal organic salt is reacted and the alkane ester product resulting from that reaction in water. Specifically, if the alkane ester product has a solubility that is less than the solubility of the reactant alkane halide, then the alkane ester product will precipitate out of the water into an insoluble layer which can be easily separated from the metallic halide which remains in the water. This separation of insoluble alkane ester from the metallic halide permits the metallic halide to be processed downstream independent from the alkane ester stream to form the metallic hydroxide required to be contacted with the alkane ester to form the alkane alcohol. If, however, the alkane ester product has a solubility that is greater than the solubility of the reactant alkane halide, the alkane ester product will not precipitate out of the water but remain with the metallic halide as a mixture in the water; making the reaction of the metallic halide into metallic hydroxide not possible. The metal organic salt may be a magnesium benzoate or a magnesium butyrate or a magnesium salicylate, for example, which are the magnesium salts of benzoic acid, butyric acid, and salicyclic acid, respectively. When magnesium butyrate is used, for example, the solubility of the ethyl bromide in water is 0.91 grams per 100 ml of water, or 0.0835 moles per 1000 ml of water and the solubility of ethyl butyrate is 0.68 grams per 100 ml of water or 0.059 moles per 1000 ml. Because the solubility of the ethyl butyrate is less than the solubility of the magnesium butyrate in water, the ethyl butyrate will precipitate out of the water as an insoluble layer according to the teachings of this disclosure. When methyl formate is used, however, the solubility of the methyl formate is greater than the solubility of the ethyl bromide and hence the methyl formate will remain with the ethyl bromide in the aqueous solution.

In one embodiment of the disclosed method of FIG. 1, the alkane is methane, the metal organic salt is magnesium formate, the halide gas is bromine gas, and the alkanol is methanol.

In an alternative embodiment with all of the disclosed methods, the disclosure provides a method of making alkanols except that the halogen gas is chlorine gas.

In an alternative embodiment with all the disclosed methods, the disclosure provides a method of making alkanols except that the halogen gas is a mixture of bromine and chlorine gasses.

In an alternative embodiment with all the disclosed methods, the disclosure provides a method of making alkanols except that the alkane is ethane.

In an alternative embodiment with all the disclosed methods, the disclosure provides a method of making alkanols except that the alkane is propane.

In an alternative embodiment with all the disclosed methods, the disclosure provides a method of making alkanols except that the alkane is butane.

In an alternative embodiment with all the disclosed methods, the disclosure provides a method of making alkanols except that the alkane is a mixture of methane and ethane.

In an alternative embodiment of FIG. 1, the invention provides a method of making alkanols except that the metal organic salt is magnesium acetate.

In an alternative embodiment of all the disclosed methods, the invention provides a method of making alkanols except that the metal organic salt is magnesium benzoate.

In an alternative embodiment of all the disclosed methods, the invention provides a method of making alkanols except that the metal organic salt is zinc benzoate.

In an alternative embodiment of FIG. 1, the invention provides a method of making alkanols except that the metal organic salt is magnesium acetate. In an alternative embodiment of FIG. 1, the invention provides a method of making alkanols except that the metal organic salt is zinc formate.

The various steps of the disclosed method may be conducted in any appropriate reactor. For example, in the disclosure of both methods, the step of oxygenating the metal halide may occur in a fluidized bed reactor, otherwise known as, a fluo-solids reactor. In some embodiments of the disclosed method the step of contacting the halogenation reaction product mixture with a metal organic salt occurs in a column packed with an inert packing material. Any one or more inert materials as are known in the art may be used in the step of contacting the halogenations reaction product mixture with a metal organic salt may be used, including for example Berl saddles. In some embodiments of the disclosed methods, the step of contacting the halogenation reaction product mixture with a metal organic salt solution occurs by flowing the halogenation reaction product mixture against a countercurrent flow of the metal organic salt.

Figure 2:
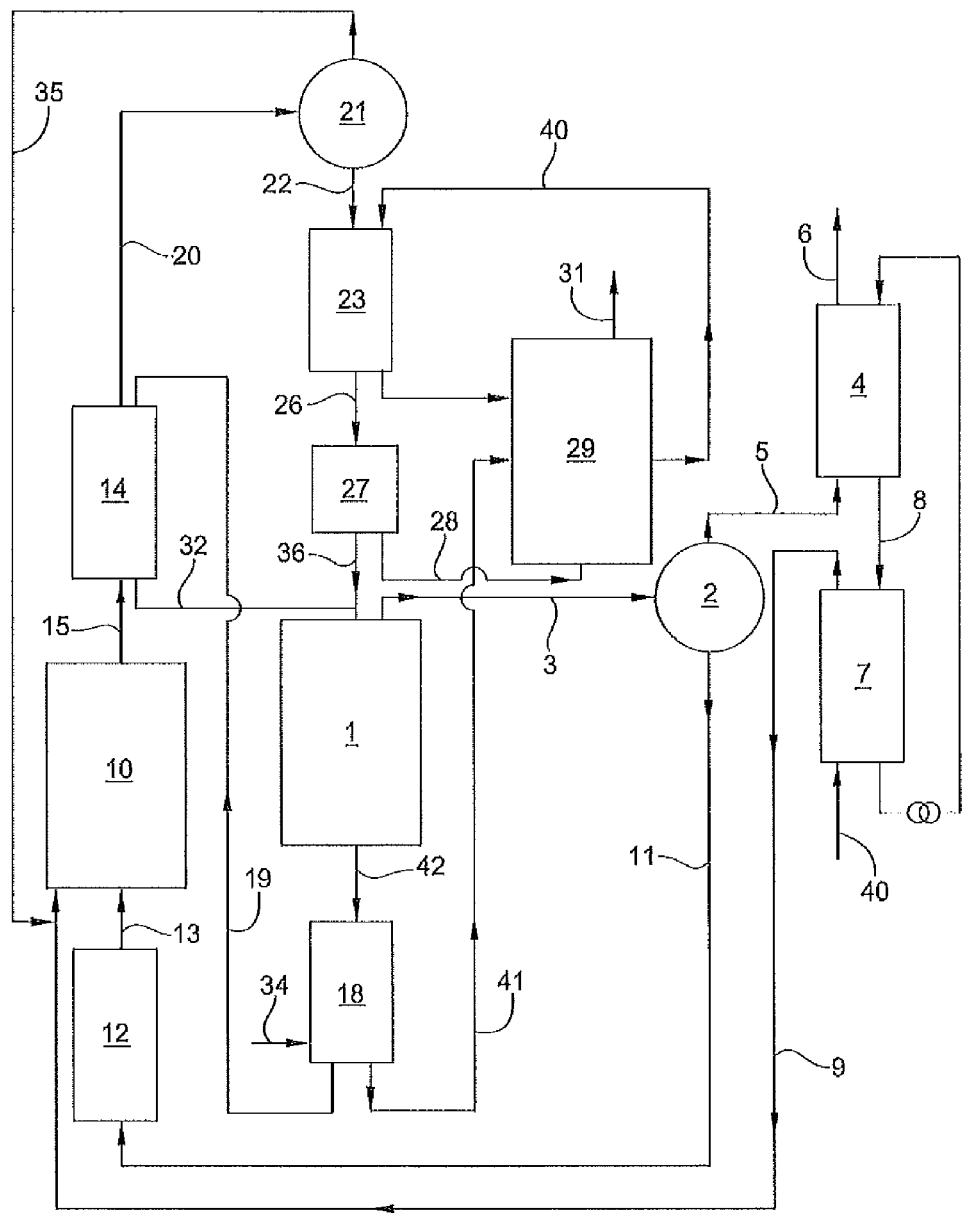
FIG. 2 is a schematic diagram of an alternative illustrative method of the disclosed process.

In some embodiments, the disclosed methods further comprises stripping the bromine from the bromine containing gasses and recycling the bromine into the halogenations reactor in the case of FIG. 1 and a brominator reactor in the case of FIG. 2.

The reactors, condensers, mixers, distillation reactor, decanter, and other equipment used in the illustrative embodiments shown in the FIGS. are well known in function and operation.

In certain embodiments of the disclosed method, the alkane to halogen gas molar ratio may be greater than 2:1. All individual values and subranges greater than a 2:1 ratio are included herein and disclosed herein; for example, the alkane to halogen gas molar ration can be from a lower limit of 2:1, 2.2:1, 2.4:1, 2.6:1, 2.8:1, 3:1, 3.5:1, 3.8:1, 4:1; 4.2:1. In at least one aspect of the present disclosure the alkane to halogen gas molar ratio is greater than or equal to 4:1. The halogenations step in all the methods wherein the alkane and halogen gas are reacted to form an alkane halide and the hydrogen halide is, in some embodiments of the disclosed methods, autocatalytic following initiation. In such embodiments, the halogenations reaction may be initiated by application of heat to a temperature between 350 and 450.degree. C. All individual values and subranges from 350 and 450.degree. C. are included herein and disclosed herein; for example, the halogenation reaction initiation temperature can be from a lower limit of 350, 360, 370, 380, 390, 400, 410, 420, 430, or 440.degree. C. to an upper limit of 360, 370, 380, 390, 400, 410, 420, 430, 440 or 450.degree. C. For example, the halogenation reaction initiation temperature may be in the range of from 350 to 380.degree. C., or in the alternative, halogenation reaction initiation temperature may be in the range of from 380 to 400.degree. C., or in the alternative, the halogenation reaction initiation temperature may be in the range of from 400 to 450.degree. C.

In alternative embodiments, the halogenations reaction may be initiated at lower temperatures in the presence of ultraviolet radiation. In such embodiments, the halogenations reaction initiation temperature may be in the range from 250 to 350.degree. C. All individual values and subranges from 250 and 350.degree. C. are included herein and disclosed herein; for example, the halogenation reaction initiation temperature can be from a lower limit of 250, 260, 270, 280, 290, 300, 310, 320, 330, or 340.degree. C. to an upper limit of 260, 270, 280, 290, 300, 310, 320, 330, 340 or 350.degree. C. for example, the halogenation reaction initiation temperature may be in the range of from 250 to 280.degree. C., or in the alternative, halogenation reaction initiation temperature may be in the range of from 280 to 300.degree. C., or in the alternative, the halogenation reaction initiation temperature may be in the range of from 300 to 350.degree. C.

Following initiation, in some embodiments of the disclosed method, the heat generated by the halogenation reaction is sufficient to maintain the halogenation reaction.

The following examples and description of the drawings is an example of one or more embodiments of the disclosed methods and is not intended to limit the scope of the disclosure.

EXAMPLES

Original Example 1

Referring to FIG. 1, natural gas comprising methane enters a mixing chamber 1 through line 2 in which it is mixed with bromine vapor entering mixing chamber 1 through line 3. The natural gas/bromine vapor mixture passes into the halogenations reactor 5 wherein methyl bromide and hydrobromic acid are formed. The halogenations reaction product mixture which may further comprise unreacted gasses passes through line 6 to condenser 7 wherein the mixture is cooled. Following cooling the halogenation reaction product mixture is passed through line 8 and flowed upward into extractor 9 through an inert packing material 10 (not shown) against a counterflow of magnesium formate solution which enters extractor 9 through line 38. Magnesium bromide is formed and magnesium bromide solution exits extractor 9 through line 11. Also formed in extractor 9 is methyl formate and formic acid gasses which exit extractor 9 through line 12.

Magnesium bromide solution enters reactor 13 wherein it is heated and reacted with oxygen entering through line 16. Bromine containing gasses are led from reactor 13 through line 17 to cooler 18 where most of the bromine is recovered and exits cooler 18 through line 19. Gasses containing traces of bromine are led from cooler 18 to absorber 20 through line 21 wherein the gasses are contacted with a counterflow of solvent, thereby recovering the remainder of the bromine Bromine free gasses may be vented or otherwise routed through line 22. The bromine containing solvent exits the bottom of absorber 20 and enters the top of stripper 23 through line 24. In the stripper 23, the bromine containing solvent is contacted with methane entering the stripper 23 through line 39, thereby stripping the bromine from the bromine containing solvent. Stripped solvent may be recovered from the bottom of stripper 23 and pumped using pump 26 through line 28 into the top of absorber 20. Magnesium oxide from oxidation reactor 13 enter reactor 29 through line 30. Water is added to reactor 29 through line 31. A slurry of magnesium oxide is formed in reactor 29 and is passed through line 32 into the top of stripper 33 wherein the magnesium oxide slurry is contacted with a counterflow of methyl formate and formic acid gasses. In stripper 33, methanol is formed and exits stripper 33 to condenser 34. Condenser 34 cools the methanol which is collected through line 35. Gas products of stripper 33 which are substantially free of methanol are passed into mixing chamber 1 through line 36. Magnesium formate solution leaves stripper 33 through line 38 through which it is passed into extractor 9.

Advantageously, the magnesium bromide, the liquid metallic halide in line 11 is separated from the liquid methyl formate, the alkane ester, under gaseous conditions in extractor 9 in Example 1 as follows:

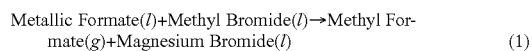

Metallic Formate(*l*)+Methyl Bromide(*l*)→Methyl Formate(*g*)+Magnesium Bromide(*l*)     (1)

In other words, the following is the condition for the separation of the alkane ester from the alkane halide in a reaction:

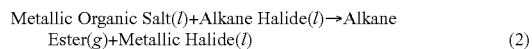

Metallic Organic Salt(*l*)+Alkane Halide(*l*)→Alkane Ester(*g*)+Metallic Halide(*l*)     (2)

which allows for the processing of the liquid magnesium bromide by oxidation reactor 13 and reactor 29 for the formation of the slurry of magnesium oxide found in line 6 required to form the methyl alkanol. More specifically, the alcohol is formed by reaction of the liquid magnesium hydroxide, the liquid metallic hydroxide in line 6, and methyl formate gas, the alkane ester gas in line 12 to form the liquid metallic salt, the metal ester in line 38, and the methanol gas, the alkane alcohol that enter condenser 34 for condensation and recover as follows:

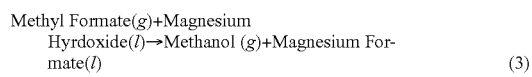

Methyl Formate(*g*)+Magnesium Hyrdoxide(*l*)→Methanol (*g*)+Magnesium Formate(*l*)     (3)

Improvement Examples

In the Improvement Examples, at the point where the alkane esters are formed from the reaction of the liquid alkane halide and the metallic organic salt in accordance with chemical equation 3 above, the reaction advantageously occurs under conditions such that the alkane esters formed are insoluble in the aqueous solution containing the liquid alkane halides and the liquid metal organic salt as the reactants. This allows for the separation of the liquid alkane esters from the liquid metallic halide so that the liquid metallic halide can be further processed into the slurry of metallic oxides that may be reacted with the liquid ester to form the alkane alcohol.

Advantageously, the alkane halides that are contacted with the metallic organic salt in the Improvement Examples are selected such that the alkane esters formed from the reaction of the alkane halide and the metallic organic salt have a solubility in water that is less than the solubility of the alkane halide in water. If the alkane ester product has a solubility that is less than the solubility of the reactant alkane halide, then the alkane ester product will precipitate out of the water into an insoluble layer which can be easily separated from the metallic halide which remains in the water. This separation of insoluble alkane ester from the metallic halide permits the metallic halide to be processed downstream independent from the alkane ester stream to form the metallic hydroxide required to be contacted with the alkane ester to form the alkane ethanol. If, however, the alkane ester product has a solubility that is greater than the solubility of the reactant alkane halide, the alkane ester product will not precipitate out of the water but remain with the metallic halide as a mixture in the water; making the reaction of the metallic halide into metallic hydroxide not possible.

Improvement Example 1

Improvement Example 1 uses the same process and equipment as shown in FIG. 1 except that equipment 9 which is an extractor in the Example 1 is replaced with a separator in Example 2 for the purpose of separating alkane esters from metal halides in the mix of products that is formed in the separator. As previously discussed, the alkane esters in Improvement Example 1 are formed from the reaction of the liquid alkane halide and the metallic organic salt, such that the reaction advantageously occurs under conditions such that the alkane esters formed are insoluble in the aqueous solution containing the liquid alkane halides and the liquid metal organic salt as the reactants. More specifically, the alkane esters formed in separator 9 in Improvement Example 1 are chosen to have a solubility in water that is less than the solubility of the alkane halide in water.

In other words, the following is the condition for the separation of the alkane ester from the alkane halide in a reaction in Improvement Example 1:

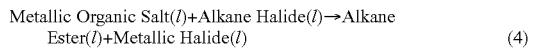

Metallic Organic Salt($l$)+Alkane Halide($l$)→Alkane Ester($l$)+Metallic Halide($l$)     (4)

As seen in chemical equation 4, the alkane ester remains as a liquid in the product mix in this reaction. In Improvement Example 1, an ethyl butyrate is used as the alkane ester. From chemical reaction 4, in Improvement Example 1, ethyl bromide is the alkane halide of choice as the alkane halide for use as a reactant to the metallic organic salt according to the following reaction occurring in separator 9:

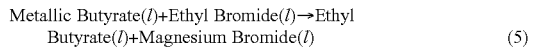

Metallic Butyrate($l$)+Ethyl Bromide($l$)→Ethyl Butyrate($l$)+Magnesium Bromide($l$)     (5)

This is because the solubility of the ethyl bromide (i.e., which reacts with the metallic organic salt to form the alkane ester according to chemical equation 5 above) in water is 0.91 grams per 100 ml of water, or 0.0835 moles per 1000 ml of water which is greater than the solubility of ethyl butyrate in water which is 0.68 grams per 100 ml of water or 0.059 moles per 1000 ml. In other words, the solubility of the ethyl butyrate (i.e., the alkane ester) in water is less than the solubility of its reactant ethyl bromide (i.e., its alkane halide reactant) in water. This advantageously keeps the ethyl butyrate in a liquid phase in separator 9. Since liquid ethyl butyrate is insoluble in water, the liquid ethyl butyrate advantageously forms an insoluble layer with the aqueous magnesium bromide solution layer. This allows the liquid ethyl butyrate to be advantageously separated in separator 9 from the magnesium bromide solution which allows the magnesium bromide solution to be processed into the magnesium oxide slurry in line 32 required for reaction with the liquid ethyl butyrate in line 12 to form the ethanol in stripper 33.

Improvement Example 2

In Improvement Example 2, an methyl benzoate is used as the alkane ester. As in Improvement Example 1, ethyl methyl benzoate is chosen as the alkane halide for use as a reactant to the metallic organic salt according to the following reaction occurring in separator 9:

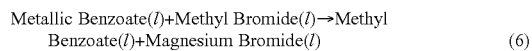

Metallic Benzoate($l$)+Methyl Bromide($l$)→Methyl Benzoate($l$)+Magnesium Bromide($l$)     (6)

This is because the solubility of methyl bromide (i.e., which reacts with the metallic organic salt to form the alkane ester according to chemical equation 6 above) in water is 0.09 grams per 100 ml of water, or 0.0094 moles per 1000 ml of water which is greater than the solubility of methyl benzoate in water which is 0.157 grams per 100 ml of water or 0.0011532 moles per 1000 ml. In other words, the solubility of the methyl benzoate (i.e., the alkane ester) in water is less than the solubility of its reactant methyl bromide (i.e., its alkane halide reactant) in water. This advantageously keeps the methyl benzoate in a liquid phase in separator 9. Since liquid methyl benzoate is insoluble in water, the liquid methyl benzoate advantageously forms an insoluble layer with the aqueous magnesium bromide solution. This allows the liquid methyl benzoate to be advantageously separated in separator 9 from the magnesium bromide solution which allows the magnesium bromide solution to be processed into the magnesium oxide slurry in line 32 required for reaction with the liquid methyl benzoate in line 12 to form the methanol in stripper 33.

Improvement Example 3

In Improvement Example 3, a methyl formate is used as the alkane ester. In this Improvement Example 3, the methyl formate is quickly seen to be an unworkable choice since the methyl halide for use as a reactant to the metallic organic salt does not follow the following reaction required to keep the alkane ester as a liquid in separator 9 according to the following teachings of my improvement disclosure:

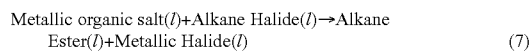

Metallic organic salt($l$)+Alkane Halide($l$)→Alkane Ester($l$)+Metallic Halide($l$)     (7)

This is because the solubility of methyl bromide (i.e., which reacts with the metallic organic salt to form the alkane ester according) in water is 0.09 grams per 100 ml of water, or 0.0094 moles per 1000 ml of water which is less than the solubility of methyl formate in water which is 30.4 grams per 100 ml of water or 5.0624479 moles per 1000 ml. In other words, the solubility of the methyl formate (i.e., the alkane ester) in water is greater than the solubility of its reactant methyl halide (i.e., its alkane halide reactant) in water. As a result, the methyl formate remains in the aqueous metal hydroxide solution in liquid separator 9 as a solvent which prevents the magnesium bromide solution to be processed into the magnesium oxide slurry in line 32 required for reaction to form the methanol. In other words, because the solubility of the methyl formate was not less than the solubility of its reactant methyl bromide, there is no methyl formate product in line 12 for use in forming the methanol in stripper 33. In contradistinction, in Example 1, there was a gaseous methyl formate product formed in line 12 for use in the methanol production reaction in stripper 33 because the extractor 9 evaporates the methyl formate from the magnesium bromide solution to create the required separation between the magnesium bromide and the methyl formate in extractor 9.

Improvement Example 4

Referring to FIG. 2, bromine is produced in fluo-solids reactor 1. The bromine vapor passes through line 3 to condenser 2 where most of the bromine, typically up to about 95%, for example, may be is condensed. The uncondensed bromine vapor passes through line 5 to absorber 4 and is flowed against a counterflow of water. Clean gasses from the cross-flow are vented to the atmosphere through line 6. Water saturated with bromine forming an aqueous bromine saturated solution passes through line 8 to extractor 7. In extractor 7, the aqueous bromine saturated solution flows against a counterflow of ethane gas which strips all, or substantially all, of the bromine from the water. The ethane containing the stripped bromine passes through line 9 to brominator reactor 10. Liquid bromine from condenser 2 passes through line 11 to vaporizer 12 where the liquid bromine is vaporized and preheated before passing through line 13 to brominator reactor 10. Bromine and ethane in brominator reactor 10 react to form ethyl bromide, ethyl dibromide, ethyl tri bromide, and hydrogen bromide gasses. These gasses exiting reactor 10 pass through line 15 to neutralizing reactor 14 where ethyl di-bromide, ethyl tri-bromide, and hydrogen bromide are neutralized with a suspension of magnesium hydroxide flowing through line 19 from reactor 18. Liquids from neutralizing reactor 14 pass through line 32 to fluo solids reactor 1. Gasses from neutralizing reactor 14 pass through line 20 to condenser 12 where the gasses are cooled.

These gases are cooled to temperatures below and preferably well below the boiling point of ethyl bromide. Liquid products from condenser 21 pass through line 22 to intensive mixer 23, which also receives magnesium benzoate or butyrate solution from reactor 29 through line 40. The liquid product from intensive mixer 23 passes through line 26 to decanter 27 where benzoate or butyrate ethyl esters separate as a substantially insoluble ester layer (phase 2 liquid) from the water layer (phase 1 liquid). The water layer containing magnesium bromide, or phase 1 liquid, flows out of decanter 27 along line 36 to reactor 1. The insoluble ester layer containing benzoate or butyrate ethyl esters, or phase 2 liquid, flows out of decanter 27 through line 28 to distillation reactor 29. At distillation reactor 29, the phase 2 insoluble ester layer contacts a suspension of magnesium hydroxide which enters distillation reactor 29 through line 41 from reactor 18. Alcohol (ethanol) from distillation reactor 29 is recovered as product through line 31. Solid product from fluo-solid reactor 1, containing magnesium oxide, flows through line 42 to reactor 18 where it contacts water entering reactor 18 from line 34 and reacts to form magnesium hydroxide. Magnesium hydroxide flows from reactor 18 to brominator reactor 10 and distillation reactor 29.

Advantageously, the alkane halides that are contacted with the metallic organic salt in intensive mixer 23 are selected such that the alkane esters formed in intensive mixer 23 have a solubility in water that is less than the solubility of the alkane halide in water. If the alkane ester product has a solubility that is less than the solubility of the reactant alkane halide, then the alkane ester product will precipitate out of the water into an insoluble layer which can be easily separated from the metallic halide which remains in the water. This separation of insoluble alkane ester from the metallic halide permits the metallic halide to be processed downstream independent from the alkane ester stream to form the metallic hydroxide required to be contacted with the alkane ester to form the alkane alcohol. If, however, the alkane ester product has a solubility that is greater than the solubility of the reactant alkane halide, the alkane ester product will not precipitate out of the water but remain with the metallic halide as a mixture in the water; making the reaction of the metallic halide into metallic hydroxide not possible. Hence, unlike Example 1 where the organic ester going to stripper 33 on line 12 is a gas, the organic ester flowing on line 28 in Example 3 from decanter 27 to distillation reactor 29 is a liquid; just as the organic ester flowing into stripper 33 on line 12 in Example 2 is a liquid. The liquid organic ester may enable the use of smaller equipment in the process, eliminate the need for a gas pump, have lower energy requirements, be less expensive and produce more alcohol output per unit volume than is possible using the method of Example 1.

Improvement Example 5

Figure 3:
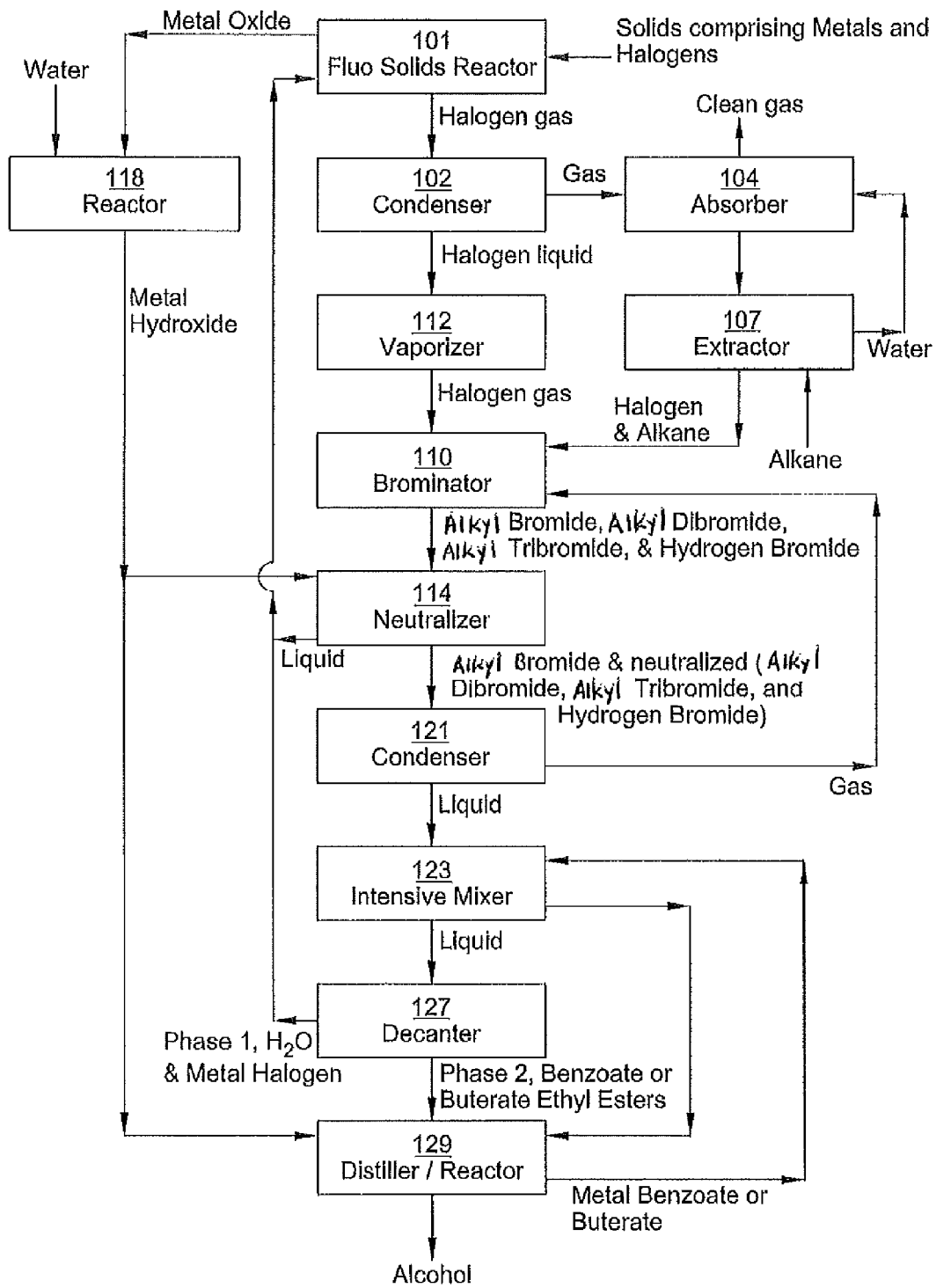
FIG. 3 is a schematic diagram of another aspect of the method of the disclosed process.

An illustrative alternative method for the production of alcohols is shown in FIG. 3 and includes the steps of reacting:

1. producing a halogen gas in a fluo-solids reactor 101, solids comprising a metal and a halogen forms a halogen gas and a metal oxide;

2. condensing the halogen gas in a condenser 102, forming a liquid halogen and a gas comprising trace halogen, the liquid halogen may be vaporized in vaporizer 112 and fed to a brominator 110;

3. recovering the trace halogen from the gas by absorbing the trace halogen in water, in absorber 104;

4. contacting an alkane to the absorbed trace halogen and water and forming a gas comprising the alkane and trace halogen (e.g. gas with an aqueous halide saturated solution), in extractor 107;

5. stripping the trace halogen from the solution to form a product mixture of an alkane and a halide;

6. feeding the product mixture of an alkane and a halide to brominator 110;

7. reacting the halogen and the alkane in brominator 110 to form halogenated alkanes;

8. reacting the metal oxide, formed in fluo solids reactor 101, with water forming a metal hydroxide in reactor 118;

9. feeding a portion of the metal hydroxide to a neutralizer 114;

10. neutralizing at least a portion of the halogenated alkanes with the metal hydroxide, forming neutralized gasses and liquids in neutralizer 114;

11. feeding the neutralized liquids to fluo solids reactor 101;

12. condensing a portion of the neutralized gasses in condenser 121 forming a condensate and a gas;

13. feeding the gas from condenser 121 to brominator reactor 110;

14. feeding the condensate from condenser 121 to intensive mixer 123;

15. mixing, in intensive mixer 123, the condensate from condenser 121 with metallic organic salt, fed from distiller/reactor 129, forming a reacted liquid;

16. decanting the reacted liquid into a first liquid phase and a second liquid phase in decanter 127 wherein the first liquid phase comprises a metal halogen and water and is fed to fluo solids reactor 101;

17. feeding the second liquid phase to distiller/reactor 129 wherein the second liquid may comprise metal hydroxide;

18. distilling and reacting of the second liquid phase in distiller/reactor 129, removing alcohol therefrom; and 19. removing the metal benzoate or butyrate from distiller/reactor 129 and feeding to the intensive mixer 123.

In at least one aspect of the process shown in FIG. 3, the metals comprised in the solids fed to fluo solids reactor 101 comprises magnesium. In this aspect the metal oxide fed to reactor 118 from fluo solids reactor 101 comprises MgO. The metal hydroxide fed to neutralizer 114 and distiller/reactor 129, from reactor 118, comprises MgOH. Additionally, the metal benzoate or butyrate fed from distiller/reactor 129 comprises magnesium benzoate or butyrate.

In at least one additional aspect of the process shown in FIG. 3, the halogens comprised in the solids fed to fluo solids reactor 101 comprises bromine. In this aspect of the process, the halogens fed to brominator 110 comprise bromine. In at least further aspect of the process shown in FIG. 3, the alkane fed to extractor 107 comprises ethane. In this aspect, the halogen and alkane fed to brominator 110, from extractor 107, comprises ethane. In yet another aspect of the process shown in FIG. 3, the halogens comprised in the solids fed to fluo solids reactor 101 comprises bromine and the metals comprised in the solids fed to fluo solids reactor 101 comprises magnesium. In this aspect, the phase 1 liquid fed to fluo solids reactor 101, from decanter 127, comprises $MgBr_2$.

As with the other Improvement Examples, the method disclosed in connection with Improvement Example 5 involves liquid phase forming of alcohol esters from liquid alkane halides and a solution of metal salts of organic acids whose alkanes esters are less soluble in water than that of the alkane halide and treating of the alcohol ester formed with magnesium or metal hydroxides to form the alcohol and the metal salt of the organic acids.

From all of the examples above and the entirety of this disclosure, the following can be seen. A method of making alcohols may involve forming of alcohol esters from liquid alkane halides and a solution of metallic salts of organic acids to produce gaseous alcohol esters for reaction with magnesium or metal hydroxides to form the alcohol and the metal salt of the organic acids. In an improvement method, liquid phase alcohol esters instead of gaseous alcohol esters are produced from liquid alkane halides and a solution of metal salts of organic acids whose alkane esters are less soluble in water than that of the alkane halide and treating of the alcohol ester formed with magnesium or metal hydroxides to form the alcohol and the metal salt of the organic acids.

INDUSTRIAL APPLICABILITY

The disclosed methods have wide use for producing alcohols from more readily available starting materials and may provide efficiencies in energy input requirements and costs over current industrial alcohol production from direct hydration of alkenes, or from cracking of appropriate fractions of distilled (or fractionated) crude oil.

More specifically, the disclosed improvement methods illustrated by the Improvement Examples in connection with FIG. 1 and the methods disclosed in connection with FIGS. 2 and 3 involve liquid phase forming of alcohol esters from liquid alkane halides and a solution of metal salts of organic acids whose alkanes esters are less soluble in water than that of the alkane halide and treating of the alcohol ester formed with magnesium or metal hydroxides to form the alcohol and the metal salt of the organic acids. In these disclosed improvement methods, the liquid organic ester may enable the use of smaller equipment in the process, eliminate the need for a gas pump, have lower energy requirements, be less expensive and produce more alcohol output per unit volume than is possible using the method of Original Example 1.

The present disclosure may be embodied in other forms without departing from the spirit and the essential attributes thereof, and, accordingly, reference should be made to the appended claims, rather than to the foregoing specification, as indicating the scope of the disclosure.

What is claimed is:

1. A method for the production of alcohols comprising:
reacting an alkane with a halogen gas to form a halogenation reaction product mixture comprising an alkane halide and a hydrogen halide, wherein the halogenation reaction product mixture is a liquid;
contacting the halogenation reaction product mixture with a metal organic salt solution, thereby forming an extractor product mixture that comprises a metal halide, an organic salt, an organic ester, and an organic acid;
separating the organic ester and the organic acid from the metal halide;
oxygenating the metal halide to form a metal oxide and a halide containing gas;
separating the metal oxide from the halide containing gas;
mixing the metal oxide with water to form a metal oxide slurry;
mixing the metal oxide slurry with a countercurrent flow that comprises the organic ester and the organic acid, thereby forming a product comprising the alcohol and a metal organic salt.

2. A method for the production of alcohols comprising:
reacting an alkane with a halogen gas to form a halogenation reaction product mixture comprising an alkane halide and a hydrogen halide;
contacting the halogenation reaction product mixture with a metal organic salt solution, thereby forming an extractor product mixture that comprises a metal halide, an organic salt, an organic ester, and an organic acid, wherein an alkane ester of the organic acid is less soluble in water than that of an alkane halide of the organic acid;
separating the organic ester and the organic acid from the metal halide;
oxygenating the metal halide to form a metal oxide and a halide containing gas;
separating the metal oxide from the halide containing gas;
mixing the metal oxide with water to form a metal oxide slurry;
mixing the metal oxide slurry with a countercurrent flow that comprises the organic ester and the organic acid, thereby forming a product comprising the alcohol and a metal organic salt.

3. The method of claim 2 wherein the alkane is methane, the halogen gas comprises at least one selected from the group consisting of bromine gas, chlorine gas, and mixtures thereof, and the alcohol is methanol.

4. The method of claim 2 wherein the alkane is ethane, the halogen gas is bromine gas, and the alcohol is ethanol.

5. The method of claim 2 wherein the metal organic salt solution comprises one selected from the group consisting of magnesium benzoate, magnesium butyrate, and a magnesium salicylate.

6. The method of claim 2 wherein the organic acid comprises at least one selected from the group consisting of benzoic acid, butyric acid, and salicyclic acid.

7. The method of claim 2 wherein the alcohol is selected from the group consisting of methanol and ethanol.

8. A method for the production of alcohols comprising:
reacting an alkane with a halogen gas to form a halogenation reaction product mixture comprising an alkane halide and a hydrogen halide;
contacting the halogenation reaction product mixture with a metal organic salt solution, thereby forming an extractor product mixture that comprises a metal halide, an organic salt, an organic ester, and an organic acid, wherein the metal organic salt solution comprises one selected from the group consisting of magnesium benzoate, magnesium butyrate, and a magnesium salicylate;
separating the organic ester and the organic acid from the metal halide;
oxygenating the metal halide to form a metal oxide and a halide containing gas;
separating the metal oxide from the halide containing gas;
mixing the metal oxide with water to form a metal oxide slurry;
mixing the metal oxide slurry with a countercurrent flow that comprises the organic ester and the organic acid, thereby forming a product comprising the alcohol and a metal organic salt.

9. The method of claim 8 wherein the alkane is methane, the halogen gas comprises at least one selected from the group consisting of bromine gas, chlorine gas, and mixtures thereof, and the alcohol is methanol.

10. The method of claim 8 wherein the alkane is ethane, the halogen gas is bromine gas, and the alcohol is ethanol.

11. The method of claim 8 wherein the alcohol is selected from the group consisting of methanol and ethanol.

12. The method of claim 1 wherein the alkane is methane, the halogen gas comprises at least one selected from the group consisting of bromine gas, chlorine gas, and mixtures thereof, and the alcohol is methanol.

13. The method of claim 1 wherein the alkane is ethane, the halogen gas is bromine gas, and the alcohol is ethanol.

14. The method of claim 1 wherein the metal organic salt solution comprises one selected from the group consisting of magnesium benzoate, magnesium butyrate, and a magnesium salicylate.

15. The method of claim 1 wherein the organic acid comprises at least one selected from the group consisting of benzoic acid, butyric acid, and salicyclic acid.

16. The method of claim 1 wherein the alcohol is selected from the group consisting of methanol and ethanol.

* * * * *